United States Patent [19]

Forber et al.

[11] Patent Number: 5,733,294
[45] Date of Patent: Mar. 31, 1998

[54] SELF EXPANDING CARDIOVASCULAR OCCLUSION DEVICE, METHOD OF USING AND METHOD OF MAKING THE SAME

[75] Inventors: Simon John Forber, Minneapolis; Richard Alan Noddin, Minnetonka, both of Minn.

[73] Assignee: B. Braun Medical, Inc., Bethlehem, Pa.

[21] Appl. No.: 608,110

[22] Filed: Feb. 28, 1996

[51] Int. Cl.$^6$ .................................................. A61B 17/00
[52] U.S. Cl. .................................................. 606/151
[58] Field of Search .................................. 606/200, 151, 606/198, 213

[56] References Cited

U.S. PATENT DOCUMENTS

| | | |
|---|---|---|
| 4,425,908 | 1/1984 | Simon . |
| 4,619,246 | 10/1986 | Molgaard-Nielsen et al. . |
| 4,832,055 | 5/1989 | Palestrant . |
| 4,994,069 | 2/1991 | Ritchart et al. . |
| 5,122,136 | 6/1992 | Guglielmi et al. . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,284,488 | 2/1994 | Sideris .............................. 606/213 |
| 5,342,348 | 8/1994 | Kaplan ............................. 606/198 X |
| 5,423,849 | 6/1995 | Engelson et al. ................ 606/198 X |
| 5,522,822 | 6/1996 | Phelps et al. ..................... 606/151 |

FOREIGN PATENT DOCUMENTS

| | | |
|---|---|---|
| 2821048 | 11/1979 | Germany . |
| WO9601591 | 1/1996 | WIPO . |

OTHER PUBLICATIONS

Target Therapeutics, Inc., *Vascular Occlusion System* brochure, Oct. 8, 1993.

*Primary Examiner*—Michael H. Thaler
*Attorney, Agent, or Firm*—Skinner and Associates; Joel D. Skinner, Jr.

[57] ABSTRACT

A self-expanding cardiovascular occlusion apparatus including a predetermined pattern of wire and three collinear bands, whereby pushing the bands together causes the two exposed braided or helical sections between them to flatten to two disk-like shapes. The disks are then forced outward relative to the middle band, causing the exposed braided or wound pattern to invaginate. The final shape is similar to two cones attached end to end. The device is heat treated to maintain this configuration. In use, the device is straightened to its cylindrical form, installed in the distal end of a device pusher which is advanced through a small diameter catheter installed in a blood vessel. When the device is expelled from the device pusher, it returns to its expanded shape and lodges in a blood vessel, for example. Once lodged in the vessel, the device will initiate thrombus formation which will occlude the vessel. The final in-situ form of the device with cone-like ends has the ability to adapt to a range of vessel sizes. The wire loops formed when the braid or helical pattern is invaginated can move relative to one another. The result is that each end of the device can conform independently to the shape of the vessel. Since the device returns to the dual-cone shape, it will resist movement in either direction when placed in a vessel. The high number of wires exposed to blood flow help increase the rate of thrombosis and help center the device within the vessel lumen. The configuration of the device also ensures that it occupies a specific predictable length when placed in a vessel, which facilitates site specific embolization. Although the primary use of the device is in embolotherapy to occlude a site in the vasculature, it may be used generally to close other sites in the cardiovascular system such as a septal defect. Methods of making and using the apparatus are also disclosed.

13 Claims, 6 Drawing Sheets

SELF EXPANDING CARDIOVASCULAR OCCLUSION DEVICE, METHOD OF USING AND METHOD OF MAKING THE SAME

BACKGROUND OF THE INVENTION

1. Field of the Invention

The present invention relates, generally to medical devices. More particularly, the invention relates to vaso-occlusion devices used in radiology, embolotherapy and the like.

2. Background Information

In embolotherapy, it is often desirable to occlude blood flow in a section of vasculature for purposes such as controlling internal bleeding, stopping blood supply to tumors, and relieving vessel-wall pressure in a region of a vessel aneurysm U.S. Pat. No. 4,994,069 describes the significant devices and methods used in the past for such purposes. They include cross-linking liquids, cyanoacrylate resins, balloons and helical wire coils. Each has significant drawbacks, but the helical wire coils seem to have found the most favor. One difficulty with these is in pushing, and, if necessary, pulling them through the catheter. The wire coil is dimensioned to engage the walls of the vessel and can be relatively stiff and difficult to advance through a catheter, especially if the blood vessel has a tortuous path. U.S. Pat. Nos. 5,226,911 and 5,250,071 describe mechanical devices that attach and detach to the coils to provide more positive pushing, pulling and positioning capability, but they are relatively complex.

Another problem with wire coils is providing enough occlusion to allow a blood clot to form. A partial solution was to coat the wire with fibers such as Dacron or cotton, but recanalization can occur by resorption of the clot by endothelial cells. The fiber coating also increases the friction with the device pusher making it more difficult to push. Another way to combine fibers and coiled wire is disclosed in U.S. Pat. No. 5,226,911 where flexible fiber loops extend outward from windings of the coil at regular intervals.

The device of U.S. Pat. No. 4,99,069 (the '069 patent) overcame many of the problems with wire coils. It provided a smaller coiled wire that when tensioned would have a linear configuration allowing it to easily be advanced through a catheter to the desired site. When the wire exited the catheter, it relaxed and took a random convoluted shape to form a space-filling mass lodged in the vessel at the site of release. However, because the final shape of the relaxed coil in the blood vessel is random, the precise location and specific length the device occupies in the vessel cannot be guaranteed.

Despite the need in the art for a vascular occlusion device which overcomes the disadvantages, shortcomings and limitations of the prior art, none insofar as is known has been developed. Accordingly, it is an object of the present invention to provide a vascular occlusion device which can occlude a blood vessel using a single device.

It is another object of the present invention to provide a vascular occlusion device which has an anchoring effect to resist movement in both directions once the device is deployed in a blood vessel.

It is another object of the present invention to provide a vascular occlusion device which can accommodate a range of blood vessel diameters.

It is another object of the present invention to provide a vascular occlusion device that creates a known length of occlusion in a blood vessel

BRIEF SUMMARY OF THE INVENTION

The present invention provides a device having a predetermined pattern of wire attached to three collinear radiopaque bands. The pattern may be braided or helically wound at a low angle. The device is formed by pushing together the three bands which causes the two exposed braided or helical sections between them to flatten to disk-like shapes similar in form to conjugate hyperbolas. Each disk is then forced outward relative to the middle band, causing the braid or helical pattern to invaginate. The final shape is similar to two cones attached end to end. The device is heat treated to maintain this configuration.

In use, the device is straightened to its cylindrical braided form, installed in the distal end of a device pusher which is advanced through a small diameter catheter installed in a blood vessel. The device is expelled from the device pusher where upon the device returns to its formed shape and lodges in the blood vessel. Once lodged in a vessel, the device will initiate thrombus formation which will occlude the vessel Since the device returns to the dual-cone shape, it will resist movement in either direction when placed in a vessel Also, the high number of wires exposed will substantially obstruct blood flow and increase the rate of thrombosis. The configuration of the device also ensures that it occupies a specific length when placed in a vessel, which facilitates site specific embolization.

The final in-situ form of the device with cone-like ends has the ability to adapt to a range of vessel sizes. The wire loops formed when the braid or helical pattern is invaginated can move relative to one another. The result is that each end of the device can conform independently to the shape of the vessel Although the primary use of the device is in embolotherapy to occlude a site in the vasculature, it may be used generally to close other sites in the cardiovascular system such as a septal defect.

The features, benefits and objects of this invention will become clear to those skilled in the art by reference to the following description, claims and drawings.

DETAILED DESCRIPTION

Figure 1:
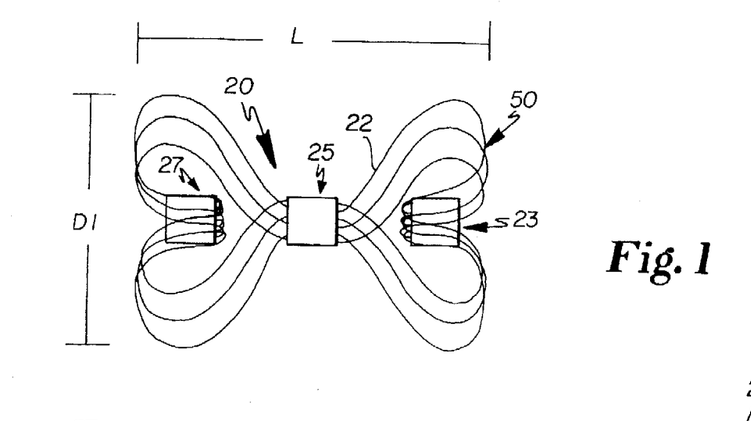
FIG. 1 is a side view of the device in its formed shape.

Referring to the drawings, wherein like reference numerals designate like or similar elements throughout, a preferred embodiment of the cardiovascular occlusion device 20 is illustrated in FIG. 1. It comprises a predetermined pattern of wires 22, preferably a braided pattern or a low angle, helically wound pattern, attached to three collinear radiopaque band assemblies 23, 25, and 27, where wires 22 have been deformed into loops 50 and heat treated to maintain a desired shape. The wires are preferably constructed of a nickel-titanium alloy called Nitinol. Shape memory polymers may alternatively be used to form wires 22. Device 20, when in its relaxed shape as shown in FIG. 1, is typically used in a vessel of somewhat smaller diameter than the diameter, D1 of device 20. Because of the flexibility of loops 50, a single device of diameter D1 can accommodate variations in vessel diameter over length L. Likewise, a single device of diameter D1 and length L can be used in a range of vessel diameters. Device 20 as shown in FIG. 1 can be made with any diameter necessary. Length L is typically, although not necessarily, greater than diameter D1. In addition, although the primary use of the device 20 is in embolotherapy to occlude a blood vessel, it may be used generally to close other sites in the cardiovascular system such as a septal defect.

The device of the preferred embodiment of FIG. 1 is made by the steps illustrated in FIGS. 2A, 2B, 3, and 4.

Figures 2A, 2B:
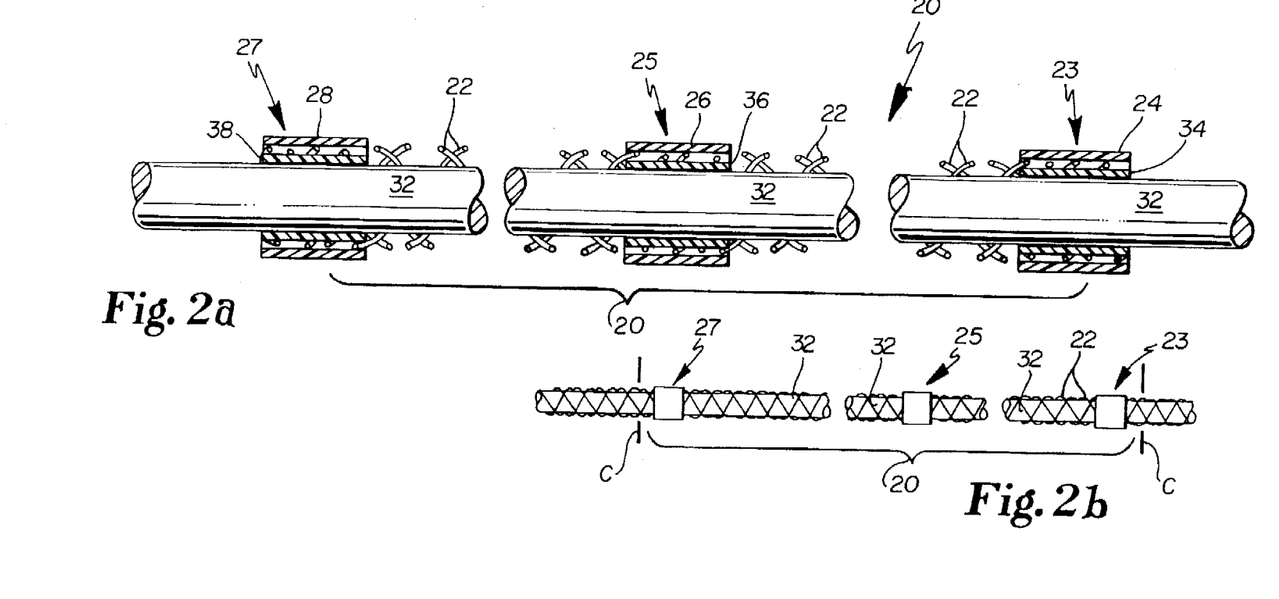
FIG. 2A shows a view partially in cross section of the wires applied to the bands in a method of making the device of FIG. 1.
FIG. 2B illustrates a method of making devices in a continuous operation.

Referring to FIG. 2A, internal radiopaque bands 34, 36, and 38, preferably made of platinum-iridinm 90/10, are installed on core 32. Other suitable band materials include titanium, pure platinum, and gold The spacing and diameter of bands 34, 36 and 38 depend on the size of the blood vessel in which device 20 will be used. The spacing between bands is typically about 1.5 times the diameter of the vessel in which device 20 will be used. Wires 22, preferably made of Nitinol, are installed onto bands 34, 36, and 38. Typical wire diameter is from 0.001 to 0.002 inches. The number of wires installed, typically between 16 and 32, depends on the wire diameter and the band diameter. Installation of wires 22 is accomplished by braiding or winding a low-angle helical pattern over core 32 with bands 34, 36 and 38 in place on core 32. Typically sixteen to thirty-two wires 0.001 to 0.002 inches diameter are braided or wound over a 0.004 to 0.020 inch core diameter at 30°-60° with respect to the axis of the core. External bands 24, 26, and 28 are slid over wires 22 and aligned with their corresponding internal bands 34, 36, and 38. Band assemblies 23, 25 and 27 are formed by unitizing each pair of internal and external bands, 24 and 34 for example, and the segments of wires 22 between them by a process such as welding, brazing, soldering, crimping or bonding. Such unitizing captures wires 22 and maintains their position axially and circumferentially with respect to bands 34, 36, and 38 on which they are installed.

A typical outer diameter of band assemblies 23, 25, and 27 is such that when device 20 is inserted in a device pusher, the pusher and device 20 can be introduced through French size catheters. For example, 0.018 inch outer diameter bands would be used for delivery through a 0.021 inch diameter working channel, and 0.034 inch outer diameter bands would be used for delivery through a 0.037 inch diameter working channel. Bands 24, 26, 28, 34, 36, and 38 typically have a wall thickness of 0.002 inches.

Referring to FIG. 2B, a typical production of devices uses many internal bands mounted on a lengthy core and the wires run continuously between them. The wires are cut at locations indicated by lines C to separate the devices 20 after the external bands and internal bands are unitized.

Figure 3:
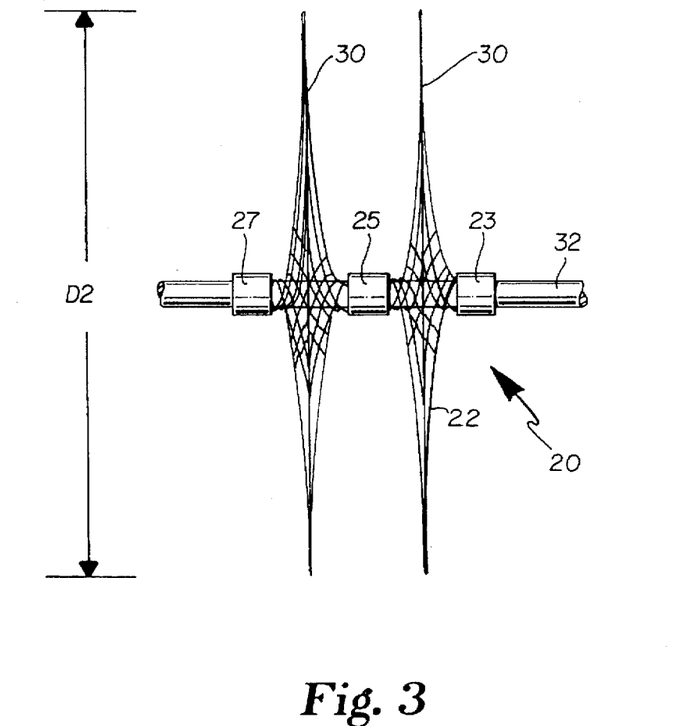
FIG. 3 shows a view of the outside bands pushed toward the center deforming the wire in a method of making the device of FIG. 1.

Referring to FIG. 3, band assemblies 23 and 27 are then slid on core 32 toward center band assembly 25 deforming wires 22 into two disk-like patterns of loops 30 of diameter D2.

Figure 4:
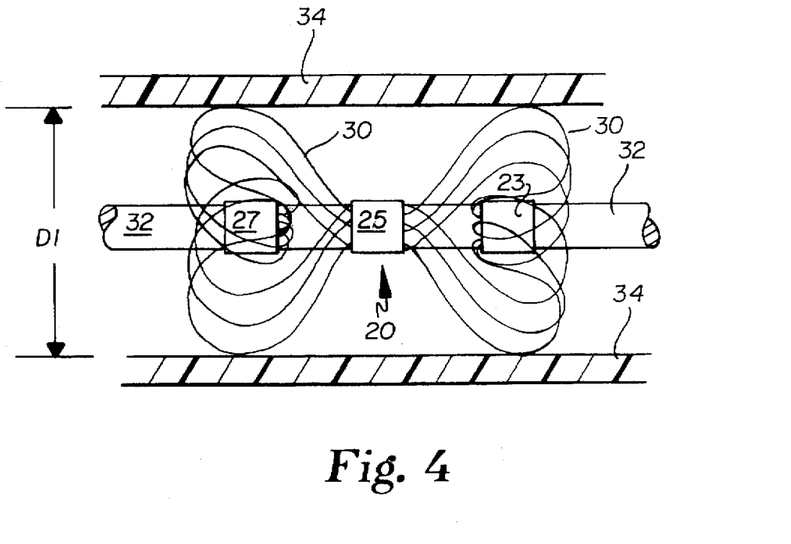
FIG. 4 shows a view partially in cross section of the device mounted in a die that forms and heat sets the loops to the desired shape in the above method.

Referring to FIG. 4, while maintaining the relative axial spacing of band assemblies 23, 25, and 27 on core 32, the device 20 is installed in a tubular die 34 with internal diameter D1, which is less than diameter D2. Device 20 and core 32 are pushed into one end of die 34 which deforms both sets of loops 30 away from the direction device 20 is being pushed. The device 20 and core 32 are slid down the entire length of die 34 until one set of loops of wires 30 exits the other end of die 34, then device 20 and core 32 are pulled back into die 34 which deforms the set of loops of wires 30 that exited die 34 in the opposite direction as the set of loops 30 that remained in die 34. This gives wires 22 the shape illustrated in FIG. 4. The device is then heat set typically at a temperature of 450° C. while in die 34 so that wires 22 will maintain their shape when removed from die 34. Device 20 and core 32 are then removed from die 34, and core 32 is then removed from device 20. Device 20 now has a relaxed shape as shown in FIG. 1 with an outer diameter of D1, the same as the inside diameter of die 34.

Figure 5A:
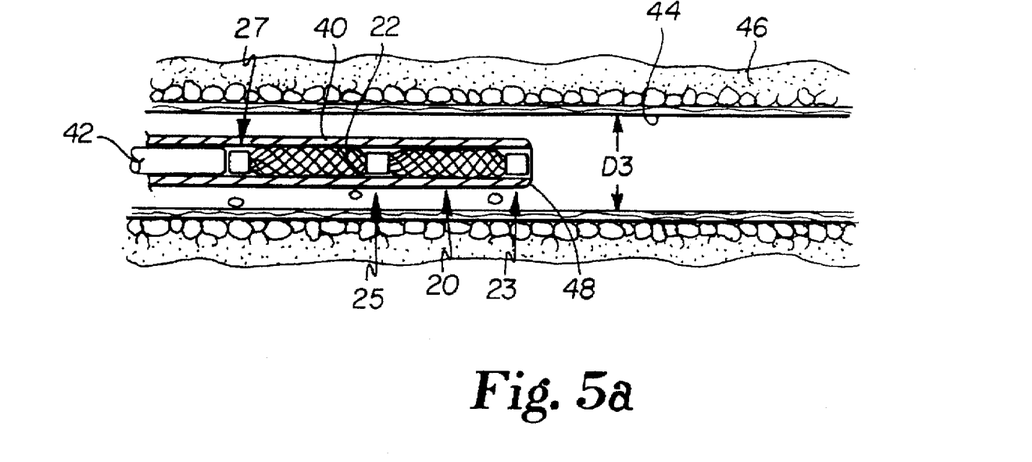
FIG. 5A shows the device of FIG. 1 installed at the distal end of a device pusher as the device is about to exit the device pusher for deployment in a blood vessel

FIGS. 5A through 5E show views partially in cross section of the way device 20 is deployed in a blood vessel 46. Referring to FIG. 5A, device 20 has been deformed to a stretched position and inserted in the distal end 48 of a device pusher 40 against pusher core 42. Device pusher 40 is a tube made of low friction material, such as Teflon®, or a material coated with a low-friction material, which has a diameter much smaller than diameter D1 of device 20 when device 20 is in a relaxed position, but larger than the outside diameter of band assemblies 23, 25, and 27. The outer diameter of device pusher 40 is such that it can be easily advanced through a small-bore catheter. Pusher core 42 is preferably a coaxial stylet comprising a central wire with a plastic overlay. The core 42 has an outer diameter such that it can easily slide inside device pusher 40. Pusher core 42 may also include a layer of Teflon® or the like.

Device 20 is stretched by pulling band assemblies 23 and 27 away from middle band assembly 25, which straightens loops of wires 22 thereby allowing device 20 to be of a diameter that will fit inside device pusher 40. Device 20 is inserted into distal end 48 of device pusher 40 so that it butts against pusher core 42. The desired site for deployment of device 20 is accessed by a small bore catheter (not shown). Device pusher 40 with device 20 installed is advanced through the catheter and into the blood vessel at the desired location for deployment of device 20. If device 20 is not already at the distal end 48 of device pusher 40, device 20 is pushed to the end 48 of device pusher 40 using pusher core 42 that pushes against band assembly 27. The diameter of device pusher 40 is small enough and the stiffness of wires 22 high enough to keep device 20 in a stretched configuration without buckling as it is pushed down device pusher 40 FIG. 5A shows device 20 at the end of device pusher 40 and about to exit out end 48 of device pusher 40. The relaxed diameter D1 of device 20 is slightly larger than the inside diameter D3 of the wall 44 of blood vessel 46 at the point of deployment.

Figure 5B:
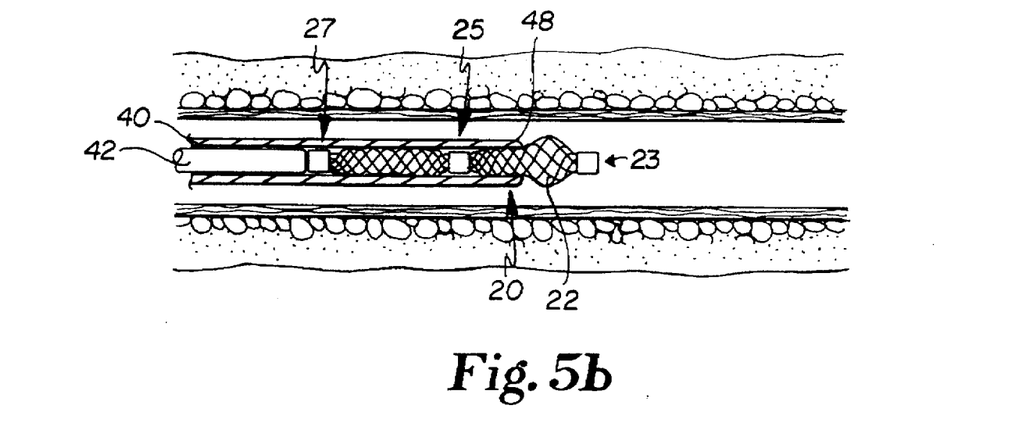
FIG. 5B shows the device beginning to emerge from the device pusher and a first end of it unfolding during deployment.

Referring to FIG. 5B which shows device 20 twenty-five percent deployed, pusher core 42 is advanced through device pusher 40 forcing device 20 out distal end 48 of device pusher 40. Band assembly 23 and part of one loop of wires 22 has exited device pusher 40. Wires 22 which have exited distal end 48 of device pusher 40 begin to return to their relaxed shape.

Figure 5C:
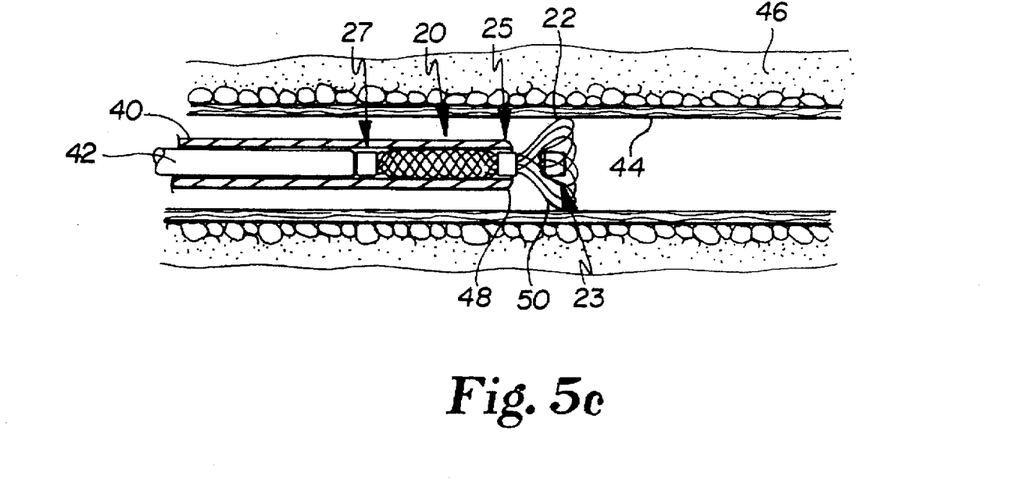
FIG. 5C shows the device half deployed.

Referring to FIG. 5C which shows device 20 fifty percent deployed, pusher core 42 is further advanced through device pusher 40 and band assembly 25 has just begun to exit distal end 48 of device pusher 40. The wires 22 that have already exited device pusher 40 have returned to their relaxed shape pulling band assembly 23 toward band assembly 25 and forming loops 50 which contact wall 44 of blood vessel 46. Because loops 50 have some freedom of movement relative to each other, they can conform, within limits, to irregularities in the shape of wall 44 of blood vessel 46.

Figure 5D:
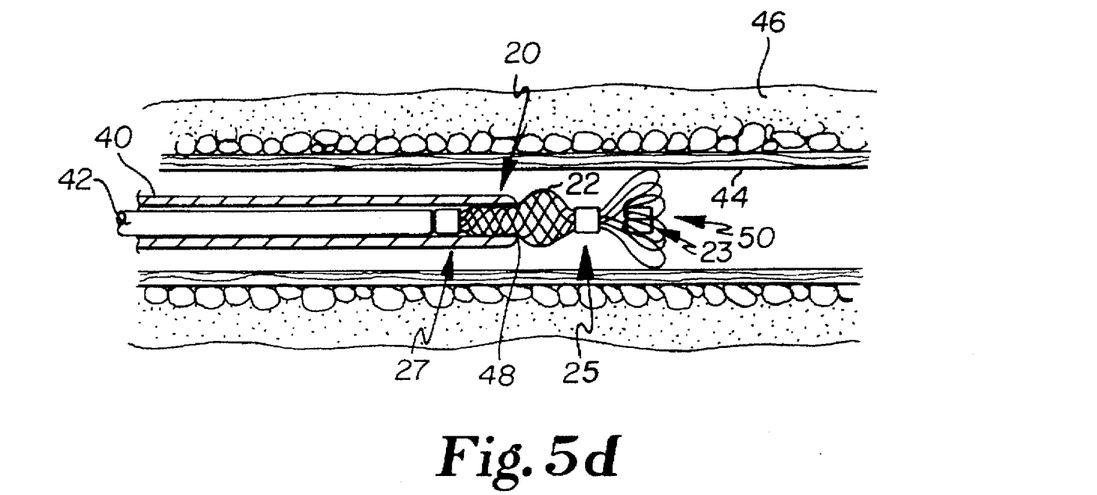
FIG. 5D shows the device ¾ deployed with a second end unfolding.

Referring to FIG. 5D which shows device 20 seventy-five percent deployed, loops 50 have contacted wall 44 of blood vessel 46. As pusher core 42 is advanced further through device pusher 40, device pusher 40 is withdrawn slightly from blood vessel 46 to allow band assembly 25 and wires 22 to exit end 48 of device pusher 40 without pushing loops 50 which have already engaged wall 44 of blood vessel 46 further into blood vessel 46. Wires 22 that are emerging from distal end 48 of device pusher 40 begin to return to their relaxed shape.

Figure 5E:
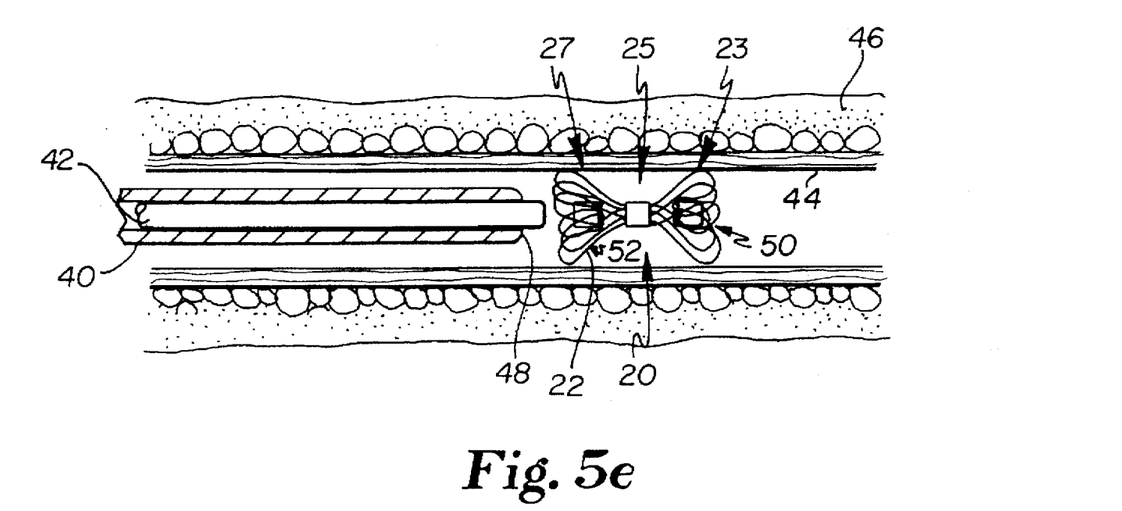
FIG. 5E shows the device fully deployed.

Referring to FIG. 5E, which shows device 20 fully deployed, pusher core 42 has been further advanced through device pusher 40 and device pusher 40 has been farther withdrawn from blood vessel 46 to allow all of wires 22 and band assembly 27 to exit end 48 of device pusher 40. Wires 22 have returned to their relaxed shape pulling band assembly 27 toward band assembly 25 and forming loops 52 which contact wall 44 of blood vessel 46. Because loops 50 and 52 project in both directions from middle band assembly 25, device 20 resists movement in both directions in blood vessel 46.

Alternatively, device 20 may be expelled from device pusher 40 by leaving pusher core 42 stationary with respect to blood vessel 46 and retracting device pusher 40 relative to pusher core 42, or the device 20 may be pushed through the catheter without the pusher 40 by a guidewire, for example.

Figure 6:
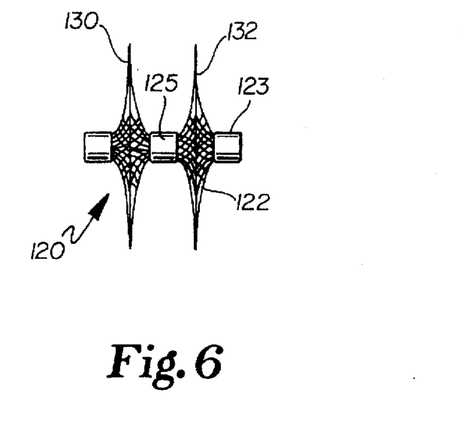
FIG. 6 is a side view of another embodiment of the device used for treating holes in the septal walls of a heart.
Figure 7:
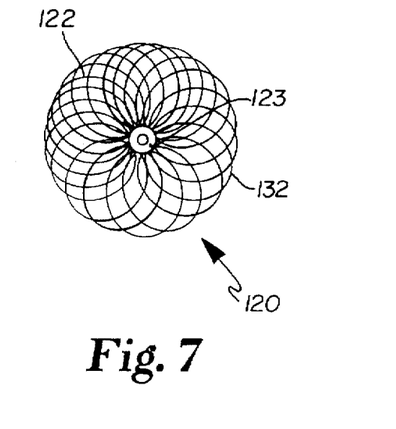
FIG. 7 is an end view of the device of FIG. 6.
Figures 8, 9:
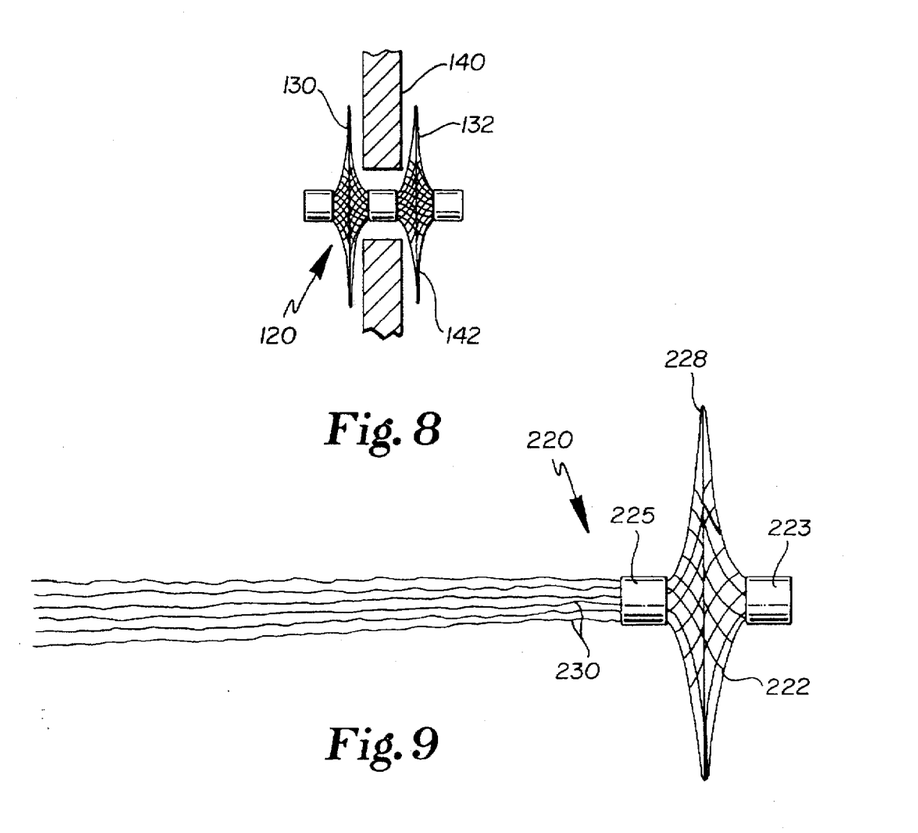
FIG. 8 shows the device of FIG. 6 fully deployed in a septal wall hole.
FIG. 9 is a side view of another embodiment of the invention used to treat berry aneurysms.

Referring to FIGS. 6, 7, and 8, an alternate embodiment 120 of the invention is as follows. Construction of device 120 begins the same way as in the preferred embodiment 20. Wires and bands are assembled identically to the preferred embodiment 20. Band assemblies 123 and 127 are pushed toward center band assembly 125 forcing wires 122 to form two disks 130 and 132 as in the preferred embodiment 20. Device 120 is heat treated at this stage to maintain its form rather than invaginating wires 122. The resulting relaxed shape of device 120 has two annular wire mesh disks 130 and 132. An end view of one of disks 130 and 132 is shown in FIG. 7. Loops of wires 122 are enmeshed with each other. The device 120 of this embodiment is used to treat holes in the septal wall of a heart. FIG. 8 illustrates the device installed in such a hole 142. Septal wall 140 is straddled by disks 130 and 132 of device 120.

Referring to FIG. 9, another embodiment 220 of the invention is as follows. Wires are fixed to only two bands rather than three bands as in the preferred embodiment 20. Device 220 is formed by forcing band assembly 223 toward band assembly 225 which forces wires 222 to form a disk-like shape 228. Device 220 is heat treated at this stage to maintain its form. In a technique described later, filaments are attached to the inside of band assemblies 223 and 225 and extended for some length beyond band assembly 225.

Figure 10:
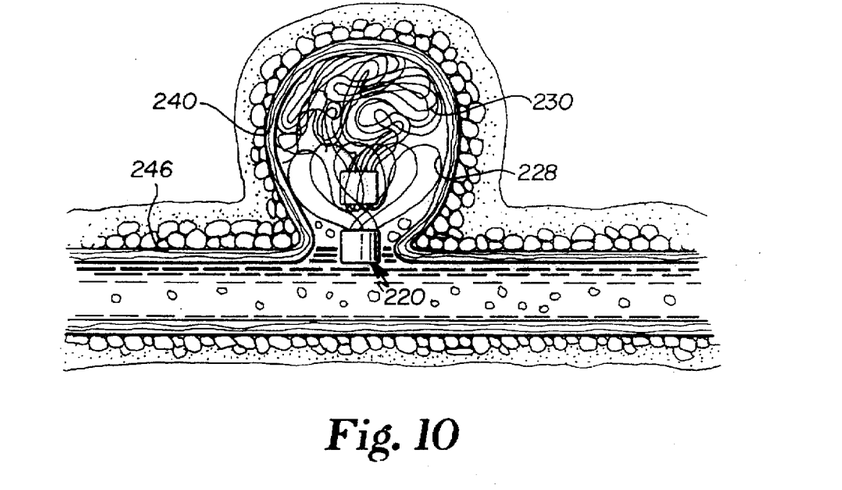
FIG. 10 is an illustration of the device of FIG. 9 installed in a berry aneurysm.

The device 220 of this embodiment is used to treat berry aneurysms, a localized aneurysm of a vessel wall characterized by a generally spherical recess extending from the side of the vessel Referring to FIG. 10, device 220 is shown deployed in a berry aneurysm 240 in a blood vessel 246. Device 220 is deployed in the same manner as with the preferred embodiment. The end of device 220 having filaments 230 extending from it is inserted into the berry aneurysm 240 first. The slack filaments become convoluted filling the aneurysm 240. The disk-like shape 228 of device 220 forms a plug to keep device 220 in aneurysm 240.

Figure 11A:
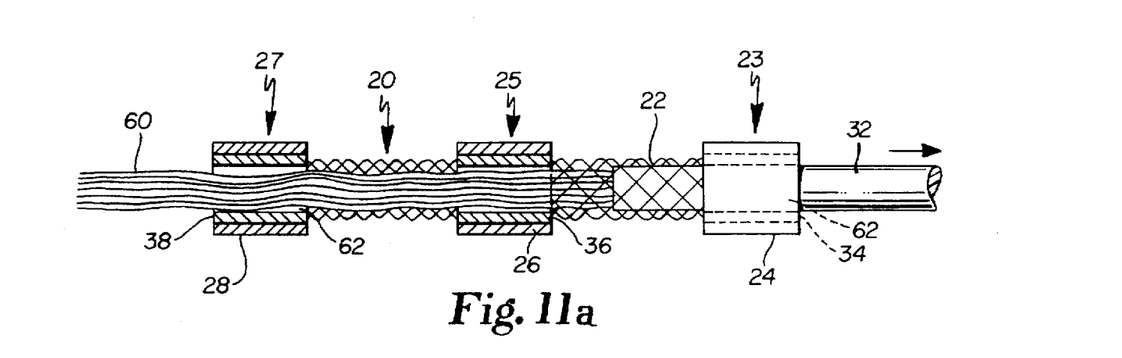
FIGS. 11A and 11B are views partially in cross section of yet another embodiment of the device where additional fibers are installed in the core of the device.
Figure 11B:
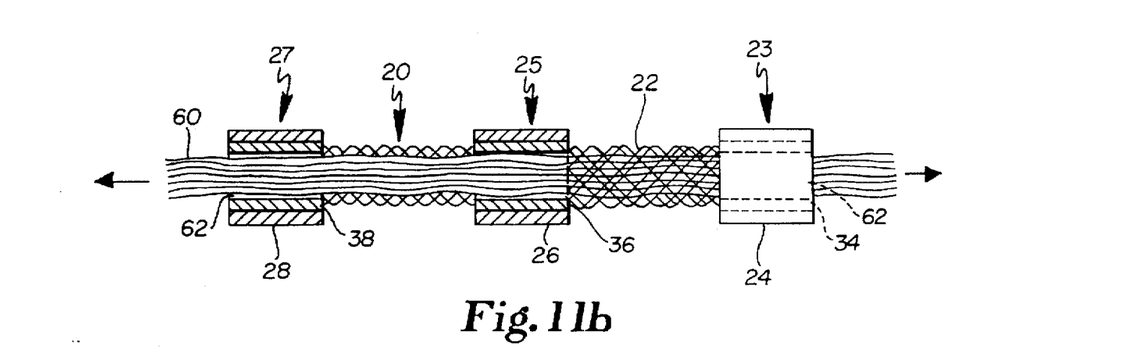

Referring to FIGS. 11A and 11B, device 20 of the preferred embodiment is shown modified as follows. After device 20 has been heat treated, core 32 is still in place. Device 20 is stretched back to its cylindrical configuration by pulling band assemblies 23 and 27 away from center band assembly 25. Referring to FIG. 11A, filaments 60, preferably polyester, in the form of yarn having a high filament to denier ratio, are attached to one end of core 32. When core 32 is removed from device 20, as indicated by the arrow, yarn filaments 60 are drawn through internal bands 34, 36, and 38 which have been unitized with their respective bands 24, 26, and 28. Referring to FIG. 11B, yarn filaments 60 are tensioned as indicated by the arrows and adhesive 62 applied to yarn filaments 60 at end bands 34 and 38. Alternatively, the filaments maybe potted. Wicking action of yarn filaments 60 pulls adhesive 62 into bands 34 and 38 where it solidifies bonding filaments 60 to bands 34 and 38. Yarn filaments 60 are cut just beyond band assemblies 23 and 27 and the cut ends of yarn filaments 60 are heated to form the yarn end to the desired finished shape, preferably rounded.

The filaments 60 are arranged within device 20 during manufacturing by applying a static electrical charge to filaments 60 before they are inserted into device 20. The charge causes filaments 60 to repel one another and uniformly distribute themselves as device 20 returns to its deployed shape. Device 20 can then be heat set to bias filaments 60 in this uniformly distributed configuration. When a device of this embodiment is deployed, the yarn filaments will buckle and splay out with wires 22, thereby causing additional mechanical obstruction of the blood vessel making the device more thrombogenic. These modifications to device 20 may also be made to the other embodiments shown and described above.

The descriptions above and the accompanying drawings should be interpreted in the illustrative and not the limited sense. While the invention has been disclosed in connection with the preferred embodiment or embodiments thereof; it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof; including both structural equivalents and equivalent structures.

What is claimed is:

1. A cardiovascular occlusion device, comprising:
   (a) three bands linearly spliced a predetermined distance from each other and defining a first end and a second end, said bands located at said first and second ends being end bands, said band disposed between said end bands being a middle band; and
   (b) a plurality of wires disposed around said bands and attached to said bands so that each wire contacts all of said bands, terminates at said end bands, and forms wire segments between said bands,
   (c) wherein the device has the following states:
      (i) a relaxed state wherein said wire segments are longer than said distance between said bands so that said wires form a set of loops between any two adjacent bands, wherein said set of loops has a first outer dimension, and wherein said set of loops forms two conical shapes, each of said conical shapes having an apex at said middle band and an invaginated base attached to one of said end bands; and
      (ii) a stretched state wherein the device has a tubular configuration having a second outer dimension which is less than said first outer dimension; and
   (d) wherein said wires have memory whereby the device returns from said stretched state to said relaxed state.

2. The cardiovascular occlusion device of claim 1, wherein each said band comprises an inner member and an outer member.

3. The cardiovascular occlusion device of claim 1 further comprising a multiplicity of filaments which:
   (a) are disposed inside all of said bands;
   (b) are attached to and span said end bands; and
   (c) have lengths between said bands which splay out inside of a shaped formed by said set of loops.

4. A cardiovascular occlusion device of claim 1 wherein said wires are disposed in a braided pattern and said loops intertwine.

5. A cardiovascular occlusion device of claim 1 wherein said wires are disposed in a helical pattern and said loops intertwine.

6. A cardiovascular occlusion device of claim 1 wherein said bands are constructed of platinum-iridium and wherein said wires are constructed of Nitinol.

7. A methodology of using the device of claim 1 to occlude a selected site in a vessel comprising the steps of:
   (a) installing a small diameter catheter in a blood vessel so that said catheter accesses the site at which said device will be deployed;
   (b) causing said device to go into its stretched state;
   (c) installing said device, while in its stretched state, into a tubular device pusher, said device pusher having an outer diameter small enough to slide inside said catheter and an inner diameter small enough so that said device cannot return to its relaxed state while inside said device pusher, but large enough so that said device can slide inside said device pusher;
   (d) advancing said device pusher through said catheter;
   (e) partially discharging said device out said device pusher at the selected site for deployment until said device partially deploys and contacts the vessel; and
   (f) retracting said device pusher slightly while simultaneously pushing said device the same distance out the end of said device pusher until said device is entirely deployed and in contact with said blood vessel.

8. A methodology of using the device of claim 1 to occlude a selected site in a vessel comprising the steps of:
   (a) installing a small diameter catheter in a blood vessel so that said catheter accesses the site at which said device will be deployed;
   (b) causing said device to go into its stretched state;
   (c) installing said device, while in its stretched state, into a tubular device pusher, said device pusher having an .outer diameter small enough to slide inside said catheter and an inner diameter small enough so that said device cannot return to its relaxed state while inside said device pusher, but large enough so that said device can slide inside said device pusher;
   (d) advancing said device pusher through said catheter; and
   (e) maintaining a position of said device relative to said blood vessel while retracting said device pusher until said device is deployed and in contact with said blood vessel.

9. A self expanding cardiovascular occlusion device comprising:
   (a) two end bands with a distance between them;
   (b) a middle band disposed along a line between said end bands and approximately equidistant from both end bands;
   (c) a plurality of wires disposed around and attached to said bands, with said wires disposed among themselves in a braided pattern and with each wire contacting all three of said bands, terminating at said end bands, and spanning sequentially from one end band, to the middle band and then to the other end band, thereby forming wire segments between said bands;
   (d) wherein said device has the following states:
      (i) a relaxed state in which said wire segments are longer than a distance between said middle band and either of said end bands so that said wires form two sets of intertwining loops, with each set of loops disposed generally between said middle braid and one of said end bands and disposed with relatively uniform spacing around an axis formed by said bands, and where each set of loops forms a cone shape having a first outer diameter, and wherein said cone shape has an apex at said middle band and an invaginated base attached to one of said end bands;
      (ii) a stretched state in which said device has a tubular configuration having a second outer diameter which is less than said first outer diameter and wherein said second outer diameter is small enough to enable said device to be pushed through a small diameter device pusher, said device pusher being of tubular configuration and small enough to be pushed through a small diameter catheter;
   (e) a multiplicity of fibers disposed inside all three bands wherein said fibers are attached to said end bands and splay out inside each of said cone shapes when said device is in its relaxed state; and
   (f) said wires having memory which returns said device from its stretched state to its relaxed state as said device is released from said device pusher thereby lodging said device in tissue at the site of release.

10. A method of making a cardiovascular occlusion device comprising the steps of:
   (a) attaching a plurality of bands at spaced intervals onto a core;
   (b) attaching a plurality of wires to said bands so that said wires span any two adjacent bands and so that said wires are disposed at circumferentially spaced intervals around said bands;

(c) applying a force to said bands to displace said bands relative to one another on said core so as to cause each of said wires to form a loop shape between any two adjacent bands wherein said loop shapes together form a three dimensional shape generally disposed between any two adjacent bands;

(d) deforming said loop shapes so that said three dimensional shape has an invaginated end;

(e) treating said wires so they will maintain their said loop shape after said force displacing said bands is removed; and (f) removing said core from said bands.

11. The method of claim 10 wherein said treating of said wires comprises a thermal treatment.

12. The method of claim 10 wherein said deforming of said loop shapes is done by installing said device in a tubular die having an internal wall which contacts said loops and thereby deforms said loops.

13. The method of claim 10 further comprising the steps of:

(a) displacing said bands back to their original position relative to one another after said wires have been treated to maintain their loop shape;

(b) threading a yarn comprising a multiplicity of filaments through the inside of said bands so that filaments are substantially collimated; and (c) attaching said yarn to each end band of said device.

* * * * *